(12) United States Patent
Krzysik et al.

(10) Patent No.: US 7,285,520 B2
(45) Date of Patent: Oct. 23, 2007

(54) WATER DISINTEGRATABLE CLEANSING WIPES

(75) Inventors: Duane G. Krzysik, Hudson, WI (US); Stephen Baldwin, Menasha, WI (US); Bernard J. Minerath, III, Oshkosh, WI (US); Beth A. Lange, Germantown, TN (US); David J. Tyrrell, Appleton, WI (US)

(73) Assignee: Kimberly-Clark Worldwide, Inc., Neenah, WI (US)

( * ) Notice: Subject to any disclaimer, the term of this patent is extended or adjusted under 35 U.S.C. 154(b) by 689 days.

(21) Appl. No.: 10/724,794

(22) Filed: Dec. 1, 2003

(65) Prior Publication Data

US 2005/0118237 A1 Jun. 2, 2005

(51) Int. Cl.
*C11D 3/00* (2006.01)
*A61F 13/00* (2006.01)

(52) U.S. Cl. ....................... 510/133; 424/443
(58) Field of Classification Search ................ 510/130, 510/131, 133, 138, 139, 140, 141, 157; 424/443
See application file for complete search history.

(56) References Cited

U.S. PATENT DOCUMENTS

| | | | |
|---|---|---|---|
| 3,227,614 A | 1/1966 | Scheuer | |
| 3,283,357 A | 11/1966 | Decker et al. | |
| 4,045,364 A | 8/1977 | Richter | |
| 4,117,187 A | 9/1978 | Adams et al. | |
| 4,164,595 A | 8/1979 | Adams et al. | |
| 4,186,233 A | 1/1980 | Krajewski et al. | |
| 4,258,849 A | 3/1981 | Miller | |
| 4,325,861 A | 4/1982 | Braun et al. | |
| 4,343,403 A | 8/1982 | Daniels et al. | |
| 4,362,781 A | 12/1982 | Anderson | |
| 4,532,063 A * | 7/1985 | Gueldenzopf | 252/186.35 |
| 4,753,844 A | 6/1988 | Jones et al. | |
| 4,792,326 A | 12/1988 | Tews | |
| 5,062,986 A * | 11/1991 | Fujita et al. | 510/152 |
| 5,076,265 A * | 12/1991 | Wokalek | 602/49 |
| 5,264,269 A | 11/1993 | Kakiuchi et al. | |
| 5,281,306 A | 1/1994 | Kakiuchi et al. | |
| 5,690,790 A | 11/1997 | Headlam et al. | |
| 5,780,418 A * | 7/1998 | Niinaka et al. | 510/439 |
| 5,935,880 A | 8/1999 | Wang et al. | |
| 6,177,391 B1 | 1/2001 | Zafar | |
| 6,429,261 B1 | 8/2002 | Lang et al. | |
| 6,444,214 B1 | 9/2002 | Cole et al. | |
| 6,495,080 B1 | 12/2002 | Tsai et al. | |
| 6,537,663 B1 | 3/2003 | Chang et al. | |
| 6,548,592 B1 | 4/2003 | Lang et al. | |
| 2002/0098994 A1 | 7/2002 | Zafar | |
| 2006/0293198 A1* | 12/2006 | Constain Ordonez | 510/141 |

FOREIGN PATENT DOCUMENTS

| | | |
|---|---|---|
| EP | 0 003 186 A | 7/1979 |
| EP | 0 896 089 A | 2/1999 |
| EP | 1 153 544 | 11/2001 |
| JP | 2001 187010 A | 7/2001 |
| WO | WO97/47227 A1 | 12/1997 |
| WO | 10-031015 | 2/1998 |
| WO | WO 00/18365 | 4/2000 |
| WO | WO 01/00023 A | 1/2001 |
| WO | 2004022684 A1 | 3/2004 |

OTHER PUBLICATIONS

International Search Report from PCT/US2004/014081 dated Oct. 19, 2004.

* cited by examiner

*Primary Examiner*—Sharon E. Kennedy
(74) *Attorney, Agent, or Firm*—Armstrong Teasdale LLP

(57) ABSTRACT

Cleansing wipes comprising a film forming polymeric material and a cleansing agent stored in dry form are disclosed. The cleansing wipes are water disintegratable such that upon contact with water, the cleansing wipes release the cleansing agent and begin to dissolve/disperse into the water. Full dissolution/dispersion of the cleansing wipes occurs in about 60 seconds or less after contact with water to allow for a sufficient time for cleansing of the hands or other skin area.

53 Claims, No Drawings

WATER DISINTEGRATABLE CLEANSING WIPES

BACKGROUND OF THE INVENTION

The present invention relates to water disintegratable cleansing wipes for cleansing the skin. More particularly, the present invention relates to water disintegratable cleansing wipes that dissolve and/or disperse after a relatively short period of time upon contact with water. The water disintegratable cleansing wipes comprise a film forming polymeric material in combination with a suitable cleansing surfactant, and dissolve and/or disperse at a suitable rate to allow for sufficient cleansing of skin, and particularly the hands.

An important hygiene habit for parents or caregivers to teach children is hand washing. Proper hand washing is an easy, quick, and effective way to prevent the transmission of bacteria, viruses, and other soils and contaminants at home, at school, and at daycare centers. Proper teaching of good hygiene habits to children can help prevent infection and illness during their early years, and can instill good sanitary habits throughout life.

The teaching of good hand washing habits to children not only includes how to effectively wash up, but also typically includes instructing a child when the appropriate times are for hand washing including, for example, after playing outside, after using the restroom, before eating, etc. As many parents and caregivers would recognize, teaching good hand washing habits to children is not an easy task. Many children are often preoccupied with other activities, making it difficult for a parent or caregiver to get the child's attention and direct them to a new task. Further, redirecting a child's attention may be even more difficult when the new task is considered by the child to be uninteresting.

In teaching good hand washing habits, parents and caregivers generally first introduce the child to the use of conventional soap and water. Although adults routinely use soap and water for hand washing, it can sometimes pose problems for a child. For example, one problem is that the child may use an inappropriate amount of soap. If the child uses too much soap, the excess soap may not be adequately rinsed away and may remain on the child's hands. Residual soap on the child's hands can be an irritant to the child's skin and eyes. Alternatively, if the child does not use a sufficient amount of soap, the hand washing may not be effective.

Another problem often encountered by parents and caregivers in teaching children good hand washing habits using conventional soap and water is that the child, if left unattended, may completely skip using the soap and simply rinse their hands with water. Failing to use soap during hand washing typically makes the washing ineffective.

Additionally, another problem encountered by parents and caregivers in teaching children to wash their hands with conventional soap and water is that it may be difficult to get the child to wash their hands for a time period sufficient to obtain effective cleansing. This problem may be compounded by the fact that it is often very difficult for children to judge how much time has elapsed during the hand washing exercise.

An alternative to the use of conventional soap and water for hand washing is the use of a conventional wet wipe that is pre-treated with a cleansing solution. Wet wipes are commonly known and used today when traditional soap and water cleansing of the face and hands is not possible, such as, for example, when traveling or camping. Wet wipes are disposable articles made from a variety of materials that have been moistened with a suitable mild surfactant-based solution. The surfactant-based solution may also include other ingredients such as antimicrobial agents, moisturizers, and skin conditioning agents.

Although wet wipes are available for cleansing of the skin, some of the problems associated with traditional soap and water hand washing are also problematic with wet wipes. First, it may be difficult to redirect the child's attention to the task of washing his or her hands with a cleansing wipe. Second, it may be difficult to get the child to wash his or her hands with the cleansing wipe for a time period sufficient for cleansing. Third, it may be difficult for the child to judge how much time has elapsed during cleansing with the wet wipe.

Another problem associated with cleansing wet wipes is that they are formed on a water-insoluble substrate and, therefore, must be disposed of in the garbage after use. Disposal of such products may be an increasing problem, and may be inconvenient in some circumstances when proper receptacles are not available.

Based on the foregoing, it is clear that there is a need for a product that can effectively clean the hands and other skin in an easy to use, efficient manner such that children can easily use the product. Additionally, it would be beneficial if the product could eliminate the need for disposal after use. Also, it would be desirable if the product could signal the user once a sufficient time period for washing had elapsed.

SUMMARY OF THE INVENTION

The present invention relates to a cleansing wipe suitable for hand washing that is stored in a dry form and is wetted with water prior to use. The cleansing wipe is a water-disintegratable wipe that uses water as a trigger to initiate dissolution and/or dispersion of the wipe and to release a surfactant or other cleaning agent for cleansing of the skin. The water-disintegratable wipe has adequate wet strength such that the wipe has an intact structure for a period of time sufficient to provide effective cleansing. Along with a surfactant cleansing agent, the cleansing wipe may additionally include other agents such as endpoint indicators, color change components, graphics, etc. to signal when a sufficient time period for washing has passed. Some endpoint indicators may provide an interesting property to keep the interest of children during hand washing to ensure effective cleansing. Additionally, cleansing wipes may include an abrasive agent, such as pumice, for cleaning especially dirty or greasy hands.

In use, a user removes the dry, water disintegratable cleansing wipe from its storage container and holds the wipe under running water. The cleansing wipe absorbs water and begins to swell, and releases the cleansing agent causing the swelling wipe to foam. The user washes his or her hands with the water-swollen cleansing wipe and, after a sufficient time has passed for cleansing, the wipe begins to dissolve and disappear, thus eliminating the need for disposal. The amount of time required for the wipe to disintegrate and its cleaning ability can be adjusted by adding one or more various fiber fillers, such as wood fiber fillers to the wipe during the manufacturing process.

Briefly, therefore, the present invention is directed to a water disintegratable cleansing wipe comprising from about 70% (by weight) to about 99% (by weight) of a substrate and from about 1% (by weight) to about 30% (by weight) of a cleansing agent. The substrate comprises a water soluble film forming polymeric material. The cleansing agent comprises a surfactant. The cleansing wipe is a single layer cleansing wipe and is capable of disintegrating upon contact with water.

The present invention is further directed to a water disintegratable cleansing wipe comprising from about 70% (by weight) to about 98% (by weight) of a substrate, from about 1% (by weight) to about 30% (by weight) of a cleansing agent, and from about 1% (by weight) to about 20% (by weight) abrasive cleansing agent. The substrate comprises a water soluble film forming polymeric material. The cleansing agent comprises a surfactant. The cleansing wipe is a single layer cleansing wipe and is capable of disintegrating upon contact with water.

The present invention is further directed to a water disintegratable cleansing wipe comprising from about 70% (by weight) to about 98% (by weight) of a substrate, from about 1% (by weight) to about 30% (by weight) of a cleansing agent, and from about 1% (by weight) to about 20% (by weight) of a fiber filler. The substrate comprises a water soluble film forming polymeric material. The cleansing agent comprises a surfactant. The cleansing wipe is a single layer cleansing wipe and is capable of disintegrating upon contact with water.

Other features and advantages of this invention will be in part apparent and in part pointed out hereinafter.

DETAILED DESCRIPTION OF THE PREFERRED EMBODIMENTS

In accordance with the present invention, it has been discovered that single layer water-disintegratable cleansing wipes can be stored in dry form until contacted with water to initiate the cleansing of the skin and the disintegration of the wipe. Surprisingly, by combining the proper amounts of a water-disintegratable film forming polymeric material and cleansing agent, the cleansing wipe has sufficient mechanical strength to effectuate thorough cleansing of the skin, yet disintegrate in water in a suitable amount of time. Additionally, endpoint indicators can also be incorporated into the cleansing wipe to alert the user when a sufficient time for cleansing has passed. Further, one or more various fiber fillers can be added to the wipe to increase mechanical strength and slow dissolution rate in water.

The water disintegratable wipes of the present invention provide a fun, easy to use hand cleansing product that can alert the user that a sufficient time for cleansing has elapsed through dissolution of the wipe alone, or in combination with an endpoint indicator. As used herein, the term "water disintegratable" means that the wipe disintegrates when contacted with water through either dissolution of the wipe into the water and/or dispersion of the wipe into the water. The water disintegratable cleansing wipes of the present invention are manufactured such that they disintegrate during use after a time for sufficiently cleansing the hands has elapsed. Although described primarily herein in combination with hand cleansing and hand cleansing wipes, it will be recognized by one skilled in the art based on the disclosure herein that the water disintegratable wipes can be used to clean other areas of the body in addition to hands, and may also be used in the shower or bath tub to effectively clean the skin.

Suitably, the water disintegratable wipes disintegrate during use in water in less than about 120 seconds, more suitably less than about 60 seconds, and still more suitably less than about 30 seconds. Such disintegration rates ensure that the cleansing agent included in the wipe has sufficient time to lather and clean the hands effectively. It should be recognized that the water disintegratable wipes may have different rates of dissolution depending upon the temperature of the water introduced onto the wipe, as well as the amount of water introduced onto the wipe. For example, if the wipe is held under constantly running water during hand washing, the wipe will typically disintegrate more rapidly than if the wipe is simply thoroughly wetted prior to use but used outside of a running stream of water. Also, the water disintegratable wipes described herein will typically dissolve more rapidly when contacted with hot water as compared to being contacted with cold water.

The water disintegratable wipe is generally rectangular in shape and may have any suitable unfolded width and length. For example, the water disintegratable wipe may have an unfolded length of from about 2.0 centimeters to about 100.0 centimeters, and desirably from about 10.0 centimeters to about 25.0 centimeters, and an unfolded width of from about 2.0 centimeters to about 80.0 centimeters and desirably from about 10.0 centimeters to about 25.0 centimeters. Typically, each individual water disintegratable wipe is arranged in a folded configuration and stacked one on top of the other to provide a stack of dry wipes. Such folded configurations are well known to those skilled in the art and include c-folded, z-folded, quarter-folded, inter-leafed, and individually stacked configurations and the like. The stack of folded wipes may be placed in the interior of a container, such as a plastic tub, to provide a package of wipes for eventual sale to the consumer. Alternatively, the wipes may include a continuous strip of material which has perforations between each wipe and which may be arranged in a stack or wound into a roll for dispensing.

Optionally, the wipe may assume a variety of shapes, including but not limited to, generally circular, oval, square, or irregularly shaped depending upon numerous factors. The size of the wipe may also vary depending upon the desired end use of the wipe.

The water disintegratable wipe may have a total basis weight of from about 25 to about 120 grams per square meter and desirably from about 40 to about 90 grams per square meter. The basis weight of the water disintegratable wipe may vary depending upon one or more desired characteristics of the wipe. For example, a suitable water disintegratable wipe designed to disintegrate in water in about 60 seconds or so may define a basis weight of from about 60 to about 80 grams per square meter and desirably about 75 grams per square meter.

As mentioned above, the water disintegratable wipes of the present invention include a substrate, which gives the wipe its structure. One suitable substrate is a water soluble film forming polymeric material. As used herein, the term "water soluble film forming polymeric material" includes materials that are water dissolvable, materials that are water dispersible, and materials that are both water dissolvable and water dispersible. The water soluble film forming polymeric material is the major component of the water disintegratable wipe and is responsible for providing the structure and mechanical strength of the wipe. The water soluble film forming polymeric material provides a relatively thick polymeric film for structure in the dry state that has sufficient mechanical strength for hand washing, yet is substantially water disintegratable upon the application of water.

The water soluble film forming polymeric material is present in the wipe in an amount of from about 70% (by weight) to about 99% (by weight), more suitable from about 70% (by weight) to about 98% (by weight), and more suitably from about 70% (by weight) to about 80% (by weight) of the water disintegratable wipe. As used herein, "by weight" refers to the total weight of the water disintegratable wipe, including all components which make up the water disintegratable wipe.

Suitable water soluble film forming polymeric materials include, for example, polyvinyl pyrrolidone-based polymers, polyethylene glycol, xantham gum, guar gum, polyquaternium polymers, pullulan, hydroxypropylmethyl cellulose, hydroxyethyl cellulose, hydroxypropyl cellulose gelatin, carboxymethyl cellulose, polyvinyl alcohol, sodium alginate, tragacanth gum, acacia gum, arabic gum, polyacrylic acid, methylmethacylate copolymer, carboxyvinyl polymer, amylase, starches, modified starches, natural starches, aluminum starch octenyl succinate, hydroxy propyl starch phosphates, high amylase starch, hydroxypropylated high amylose starch, dextrin, pectin, chitan, chitosan, levan, elsinan, collagen, zein, glutan, soy protein isolate, whey protein isolate, casein, locust bean gum, karaya gum, carrageenan, gellan, agar, algin, furcellaran, polyhydroxy acid polymers, and mixtures thereof. Particularly suitable water soluble film forming polymeric materials include starches, modified starches, natural starches, aluminum starch octenyl succinate, and hydroxy propyl starch phosphates.

The water disintegratable wipes of the present invention also include a cleansing agent for cleansing the skin. In one embodiment, the cleansing agent is a suitable foaming surfactant material. The cleansing agent provides the foaming, lathering, and cleansing properties of the disintegratable wipes once contacted with water. The cleansing agent is present in the water disintegratable wipes of the present invention in an amount of from about 1% (by weight) to about 30% (by weight), suitably from about 20% (by weight) to about 30% (by weight).

Suitable surfactant cleansing agents include, for example, anionic surfactants, nonionic surfactants, betaines, sultaines, amphoterics, zwitterionic surfactants, imidazolines, sulfosuccinates, amineoxides, alkanolamides, sugar surfactants, metal soaps, and combinations thereof. Particularly suitable surfactant cleansing agents include betaines and sulfosuccinates. It is generally preferred that the surfactant cleansing agent be a mild surfactant cleansing agent.

Some suitable cleansing agents, including many foaming surfactants, may produce very large bubbles during the foaming and lathering of the surfactant during use of the water disintegratable wipes of the present invention. Although this does not degrade the efficacy of the wipe product and its ability to clean skin, it can be undesirable in some circumstances. As such, in one embodiment of the present invention, the water disintegratable wipes may include a foam stabilizer agent or combination of foam stabilizer agents to reduce the size of bubbles produced by the cleansing agent after the wetting of the water disintegratable wipe during use. The foam stabilizer agent may be present in the water disintegratable wipes of the present invention in an amount of from about 1% (by weight) to about 5% (by weight). At this level, the foam stabilizer agent can reduce and control the size of the bubbles formed by the cleansing agent during use of the product.

Suitable foam stabilizing agents include, for example, alkanolamides, polyethylene glycols, polyols, PEG dimethicones, ethoxylated fatty alcohols and combinations thereof.

In some circumstances, it may be desirable to utilize a water disintegratable cleansing wipe having increased strength and durability and requiring an increased time period for disintegration of the wipe in water. For example, if the water disintegratable wipes were to be used on exceptionally dirty hands, or hands containing grease or other hard to remove contaminants, a wipe having increased mechanical strength and durability may be desirable. To provide a water disintegratable wipe having increased strength and durability, and requiring a longer time period for dissolution in water, the wipe may include one or more natural or synthetic fibers for use as fillers. Such natural or synthetic fibers will typically increase the mechanical strength and durability of the wipe, and cause the wipe to require an increased amount of time for disintegration into water. Also, the filler fibers may increase the cleansing ability of the wipe as they may tend to be slightly abrasive on the skin when used. Depending on the desired increase in mechanical strength and durability, the fiber filler may be included in the water disintegratable wipe in an amount of from about 1% (by weight) to about 20% (by weight). Suitable fiber fillers include, for example, soft wood fibers, hard wood fibers, non-wood vegetable fibers, and combinations thereof.

In some embodiments it may be desirable to utilize a plasticizing agent to reduce the stiffness or rigidity of the water disintegratable cleansing wipe. In some embodiments, the water disintegratable may be somewhat stiff, and may crack during shipment or use prior to being wetted with water. In order to reduce stiffness and prevent the introduction of cracks onto the surface of the wipe, from about 1% (by weight) to about 15% (by weight), suitably from about 5% (by weight) to about 10% (by weight) of a plasticizing agent may be added to the wipe during manufacturing. Suitable plasticizing agents for inclusion in the wipe formulation include, for example, glycerin, diglycerin, sorbitol, propylene glycol, butylene glycol, ethylene glycol, hydrogenate starch hydrolysates, low molecular weight polyethylene glycols, silicone glycols, and the like and combinations thereof.

In another embodiment, the water disintegratable wipes described herein may comprise an abrasive agent to further improve the cleansing ability of the cleansing agent included in the wipe. The abrasive agent included in the water disintegratable wipe mildly scours the skin surface in combination with the surfactant to aid the cleansing agent in the removal of embedded soils, such as grease. The abrasive agent may be present in the water disintegratable wipe in an amount of from about 1% (by weight) to about 20% (by weight). Suitable abrasive agents include, for example, pumice, polyethylene beads, silica, diatomaceous earth, nylon 12 beads, polymethacrylate polymers, nut shells, and clays.

In another embodiment of the present invention, the water disintegratable wipes may include an endpoint indicator to alert the user that a sufficient amount of time has elapsed for washing of the hands. The endpoint indicator is used in combination with the disintegration of the wipe to alert the user as the endpoint indicator appears just prior to the initial disintegration of the water disintegratable wipe. Suitable endpoint indicators include, for example, hidden graphic images that appear after sufficient time has elapsed, color changes that occur after sufficient time has elapsed, and the occurrence of a fizzing or crackling after sufficient time has elapsed. In one embodiment, a hidden graphic image is used on water disintegratable wipes suitable for children's use as the hidden graphic image helps focus the child's attention on the hand washing as he or she knows that, at some point, a graphic image will appear. Alternatively, a salt such as calcium chloride can be incorporated into the water disintegratable wipe to cause a crackling sensation at the appropriate time.

Along with the components comprising the water disintegratable wipes described herein, the wipes may additionally comprise a suitable amount of various optional components to impart additional specific benefits to the wipe. Specific examples of optional skin health components include, for example, antimicrobials, humectants, moisturizers, fragrances, skin conditioning agents, lipids, botanicals, vitamin E and other vitamins, aloe, and combinations thereof.

The water disintegratable wipes of the present invention may be manufactured using the process described herein. As one skilled in the art will recognize based on the disclosure herein, modifications to the manufacturing process can be made to adjust the resulting properties of the wipes without departing from the scope of the present invention.

In one embodiment, the water disintegratable wipes can be manufactured by introducing the water-soluble film forming polymeric material and cleansing agent (a foaming surfactant, for example) into deionized water. Any other optional components, such as foam stabilizers or fiber fillers, for example, can also be added to the deionized water. The deionized water may be heated to a temperature of from about 25° C. to about 50° C. to improve the dissolution rate of the components. Once introduced into the deionized water, the components are thoroughly mixed and allowed to hydrate and swell in the water for a period of from about 24 hours to about 48 hours, to form a gel-like material. The amount of water utilized to prepare the gel-like material is not critical, and is typically sufficient to produce a gel comprising from about 40% (by weight) to about 80% (by weight) water. The resulting gel-like material is chilled to a temperature of from about 20° C. to about 30° C. for from about 1 hour to about 48 hours.

After the gel-like material has been chilled for a sufficient period, the resulting gel mixture is cast onto a suitable film forming wire, tray, mold or substrate and dried. The wire, tray, mold of substrate should have a surface tension that allows the resulting gel mixture to spread evenly across the substrate without the formation of a destructive bond between the mixture and the substrate. Suitable substrates include glass, stainless steel, Teflon, and polyethylene-impregnated paper. Drying of the mixture may be carried out at high temperatures using a drying oven, drying terminal, vacuum drier, or any other suitable drying equipment which does not adversely affect the components of the mixture. The resulting thin, dry polymer film may comprise up to about 10% moisture. The dried film is then segmented into individual units by die-cutting or slitting and die-cutting.

In another embodiment, the water disintegratable wipes can be manufactured by introducing only the water-soluble film forming polymeric material into deionized water. The deionized water may be heated to a temperature of from about 25° C. to about 50° C. to improve the dissolution rate of the polymeric material. Once introduced into the deionized water, the polymeric material is thoroughly mixed and allowed to hydrate and swell in the water for a period of from about 24 hours to about 48 hours, to form a gel-like material. The amount of water utilized to prepare the gel-like material is not critical, and is typically sufficient to produce a gel comprising from about 40% (by weight) to about 80% (by weight) water. The resulting gel-like material is chilled to a temperature of from about 20° C. to about 30° C. for from about 1 hour to about 48 hours.

After the gel-like material has been chilled for a sufficient period, the resulting gel mixture is cast onto a suitable film forming wire, tray, mold or substrate and dried. The wire, tray, mold or substrate should have a surface tension that allows the resulting gel mixture to spread evenly across the substrate without the formation of a destructive bond between the mixture and the substrate. Suitable substrates include glass, stainless steel, Teflon, and polyethylene-impregnated paper. Drying of the mixture may be carried out at high temperatures using a drying oven, drying terminal, vacuum drier, or any other suitable drying equipment which does not adversely affect the resulting product. The resulting thin, dry polymer film may comprise up to about 10% moisture. After drying, the cleansing agent (such as a foaming surfactant) and any other optional components may be introduced onto the dried polymer film through one of various mechanisms known in the art such as, for example, spraying, printing, spreading and the like. The dried film comprising the cleansing agent and any optional components is then segmented into individual units by die-cutting or slitting and die-cutting.

In view of the above, it will be seen that the several objects of the invention are achieved. As various changes could be made in the above-described water disintegratable wipes without departing from the scope of the invention, it is intended that all matter contained in the above description be interpreted as illustrative and not in a limiting sense.

What is claimed is:

1. A water disintegratable cleansing wipe comprising from about 70% (by weight) to about 99% (by weight) of a substrate and from about 1% (by weight) to about 30% (by weight) of a cleansing agent, the substrate being a water soluble film forming polymeric material and the cleansing agent comprising a surfactant material, wherein the cleansing wipe is a single layer cleansing wipe and is capable of disintegrating upon contact with water.

2. The water disintegratable cleansing wipe as set forth in claim 1 wherein the wipe comprises from about 70% (by weight) to about 80% (by weight) of the substrate and from about 20% (by weight) to about 30% (by weight) of the cleansing agent.

3. The water disintegratable cleansing wipe as set forth in claim 2 further comprising a plasticizing agent.

4. The water disintegratable cleansing wipe as set forth in claim 1 wherein the wipe has a material basis weight of from about 25 grams/square meter to about 120 grams/square meter.

5. The water disintegratable cleansing wipe as set forth in claim 1 wherein the wipe has a material basis weight of from about 40 grams/square meter to about 90 grams/square meter.

6. The water disintegratable cleansing wipe as set forth in claim 1 wherein the wipe is capable of disintegrating in water in less than about 120 seconds.

7. The water disintegratable cleansing wipe as set forth in claim 1 wherein the wipe is capable of disintegrating in water in less than about 60 seconds.

8. The water disintegratable cleansing wipe as set forth in claim 1 wherein the wipe is capable of disintegrating in water is less than about 30 seconds.

9. The water disintegratable cleansing wipe as set forth in claim 1 wherein the film forming polymeric material is selected from the group consisting of polyvinyl pyrrolidone-based polymers, polyethylene glycol, xantham gum, guar gum, polyquaternium polymers, pullulan, hydroxypropylmethyl cellulose, hydroxyethyl cellulose, hydroxypropyl cellulose gelatin, carboxymethyl cellulose, polyvinyl alcohol, sodium alginate, tragacanth gum, acacia gum, arabic gum, polyacrylic acid, methylmethacylate copolymer, carboxyvinyl polymer, amylase, starches, modified starches, natural starches, aluminum starch octenyl succinate, hydroxy propyl starch phosphates, high amylase starch, hydroxypropylated high amylose starch, dextrin, pectin, chitan, chitosan, levan, elsinan, collagen, zein, glutan, soy protein isolate, whey protein isolate, casein, locust bean gum, karaya gum, carrageenan, gellan, agar, algin, furcellaran, polyhydroxy acid polymers, and mixtures thereof.

10. The water disintegratable cleansing wipe as set forth in claim 1 wherein the film forming polymeric material is selected from the group consisting of starches, modified starches, natural starches, aluminum starch octenyl succinate, and hydroxy propyl starch phosphates.

11. The water disintegratable cleansing wipe as set forth in claim 1 wherein the surfactant material is selected from the group consisting of anionic surfactants, nonionic surfactants, betaines, sultaines, amphoterics, zwitterionic surfactants, imidazolines, sulfosuccinates, amineoxides, alkanolamides, sugar surfactants, metal soaps, and combinations thereof.

12. The water disintegratable cleansing wipe as set forth in claim 1 wherein the surfactant material is selected from the group consisting of betaines and sulfosuccinates.

13. The water disintegratable cleansing wipe as set forth in claim 1 further comprising a skin health benefit ingredient selected from the group consisting of antimicrobials, moisturizers, humectants, fragrances, vitamin E, aloe, lipids, botanicals, and combinations thereof.

14. The water disintegratable cleansing wipe as set forth in claim 1 further comprising an endpoint indicator.

15. The water disintegratable cleansing wipes as set forth in claim 14 wherein the endpoint indicator is selected from the group consisting of a coloring agent and a graphic.

16. The water disintegratable cleansing wipe as set forth in claim 1 further comprising from about 1% (by total weight) to about 5% (by total weight) of a foam stabilizer.

17. The water disintegratable cleansing wipe as set forth in claim 16 wherein the foam stabilizer is selected from the group consisting of alkanolamides, polyethylene glycols, polyols, PEG dimethicones, ethoxylated fatty alcohols, and combinations thereof.

18. A water disintegratable cleansing wipe comprising from about 70% (by weight) to about 98% (by weight) of a substrate, from about 1% (by weight) to about 30% (by weight) of a cleansing agent, and from about 1% (by weight) to about 20% (by weight) abrasive cleansing agent, the substrate being a water soluble film forming polymeric material and the cleansing agent comprising a surfactant material, wherein the cleansing wipe is a single layer cleansing wipe and is capable of disintegrating upon contact with water.

19. The water disintegratable cleansing wipe as set forth in claim 18 wherein the abrasive cleansing agent is selected from the group consisting of pumice, silica, diatomaceous earth, polyethylene beads, nylon 12 beads, polymethacrylate polymers, nut shells, and clays.

20. The water disintegratable cleansing wipe as set forth in claim 18 wherein the wipe comprises from about 70% (by weight) to about 80% (by weight) of the substrate and from about 20% (by weight) to about 30% (by weight) of the cleansing agent.

21. The water disintegratable cleansing wipe as set forth in claim 18 wherein the wipe has a material basis weight of from about 25 grams per square meter to about 120 grams per square meter.

22. The water disintegratable cleansing wipe as set forth in claim 18 wherein the wipe has a material basis weight of from about 40 grams per square meter to about 90 grams per square meter.

23. The water disintegratable cleansing wipe as set forth in claim 18 wherein the wipe is capable of disintegrating in water in less than about 120 seconds.

24. The water disintegratable cleansing wipe as set forth in claim 18 wherein the wipe is capable of disintegrating in water in less than about 60 seconds.

25. The water disintegratable cleansing wipe as set forth in claim 18 wherein the wipe is capable of disintegrating in water is less than about 30 seconds.

26. The water disintegratable cleansing wipe as set forth in claim 18 wherein the film forming polymeric material is selected from the group consisting of polyvinyl pyrrolidone-based polymers, polyethylene glycol, xantham gum, guar gum, polyquaternium polymers, pullulan, hydroxypropylmethyl cellulose, hydroxyethyl cellulose, hydroxypropyl cellulose gelatin, carboxymethyl cellulose, polyvinyl alcohol, sodium alginate, tragacanth gum, acacia gum, arabic gum, polyacrylic acid, methylmethacylate copolymer, carboxyvinyl polymer, amylase, starches, modified starches, natural starches, aluminum starch octenyl succinate, hydroxy propyl starch phosphates, high amylase starch, hydroxypropylated high amylose starch, dextrin, pectin, chitan, chitosan, levan, elsinan, collagen, zein, glutan, soy protein isolate, whey protein isolate, casein, locust bean gum, karaya gum, carrageenan, gellan, agar, algin, furcellaran, polyhydroxy acid polymers, and mixtures thereof.

27. The water disintegratable cleansing wipe as set forth in claim 18 wherein the film forming polymeric material is selected from the group consisting of starches, modified starches, natural starches, aluminum starch octenyl succinate, and hydroxy propyl starch phosphates.

28. The water disintegratable cleansing wipe as set forth in claim 18 wherein the surfactant material is selected from the group consisting of anionic surfactants, nonionic surfactants, betaines, sultaines, amphoterics, zwitterionic surfactants, imidazolines, sulfosuccinates, amineoxides, alkanolamides, sugar surfactants, metal soaps, and combinations thereof.

29. The water disintegratable cleansing wipe as set forth in claim 18 wherein the surfactant material is selected from the group consisting of betaines and sulfosuccinates.

30. The water disintegratable cleansing wipe as set forth in claim 18 further comprising a skin health benefit ingredient selected from the group consisting of antimicrobials, moisturizers, humectants, fragrances, vitamin E, aloe, lipids, botanicals, and combinations thereof.

31. The water disintegratable cleansing wipe as set forth in claim 18 further comprising an endpoint indicator.

32. The water disintegratable cleansing wipe as set forth in claim 18 wherein the endpoint indicator is selected from the group consisting of a coloring agent and a graphic.

33. The water disintegratable cleansing wipe as set forth in claim 18 further comprising from about 1% (by total weight) to about 5% (by total weight) of a foam stabilizer.

34. The water disintegratable cleansing wipe as set forth in claim 33 wherein the foam stabilizer is selected from the group consisting of alkanolamides, polyethylene glycols, polyols, PEG dimethicones, ethoxylated fatty alcohols, and combinations thereof.

35. A water disintegratable cleansing wipe comprising from about 70% (by weight) to about 98% (by weight) of a substrate, from about 1% (by weight) to about 30% (by weight) of a cleansing agent, and from about 1% (by weight) to about 20% (by weight) fiber filler, the substrate being a water soluble film forming polymeric material and the cleansing agent comprising a surfactant material, wherein the cleansing wipe is a single layer cleansing wipe and is capable of disintegrating upon contact with water.

36. The water disintegratable cleansing wipe as set forth in claim 35 wherein the wipe comprises from about 70% (by weight) to about 80% (by weight) of the substrate and from about 20% (by weight) to about 30% (by weight) of the cleansing agent.

37. The water disintegratable cleansing wipe as set forth in claim 35 wherein the wipe has a material basis weight of from about 25 grams per square meter to about 120 grams per square meter.

38. The water disintegratable cleansing wipe as set forth in claim 35 wherein the wipe has a material basis weight of from about 40 grams per square meter to about 90 grams per square meter.

39. The water disintegratable cleansing wipe as set forth in claim 35 wherein the wipe is capable of disintegrating in water in less than about 120 seconds.

40. The water disintegratable cleansing wipe as set forth in claim 35 wherein the wipe is capable of disintegrating in water in less than about 60 seconds.

41. The water disintegratable cleansing wipe as set forth in claim 35 wherein the wipe is capable of disintegrating in water in less than about 30 seconds.

42. The water disintegratable cleansing wipe as set forth in claim 35 wherein the film forming polymeric material is selected from the group consisting of polyvinyl pyrrolidone-based polymers, polyethylene glycol, xantham gum, guar gum, polyquaternium polymers, pullulan, hydroxypropylmethyl cellulose, hydroxyethyl cellulose, hydroxypropyl cellulose gelatin, carboxymethyl cellulose, polyvinyl alcohol, sodium alginate, tragacanth gum, acacia gum, arabic gum, polyacrylic acid, methylmethacylate copolymer, carboxyvinyl polymer, amylase, starches, modified starches, natural starches, aluminum starch octenyl succinate, hydroxy propyl starch phosphates, high amylase starch, hydroxypropylated high amylose starch, dextrin, pectin, chitan, chitosan, levan, elsinan, collagen, zein, glutan, soy protein isolate, whey protein isolate, casein, locust bean gum, karaya gum, carrageenan, gellan, agar, algin, furcellaran, polyhydroxy acid polymers, and mixtures thereof.

43. The water disintegratable cleansing wipe as set forth in claim 35 wherein the film forming polymeric material is selected from the group consisting of starches, modified starches, natural starches, aluminum starch octenyl succinate, and hydroxy propyl starch phosphates.

44. The water disintegratable cleansing wipe as set forth in claim 35 wherein the surfactant material is selected from the group consisting of anionic surfactants, nonionic surfactants, betaines, sultaines, amphoterics, zwitterionic surfactants, imidazolines, sulfosuccinates, amineoxides, alkanolamides, sugar surfactants, metal soaps, and combinations thereof.

45. The water disintegratable cleansing wipe as set forth in claim 35 wherein the surfactant material is selected from the group consisting of betaines and sulfosuccinates.

46. The water disintegratable cleansing wipe as set forth in claim 35 further comprising a skin health benefit ingredient selected from the group consisting of antimicrobials, moisturizers, humectants, fragrances, vitamin E, aloe, lipids, botanicals, and combinations thereof.

47. The water disintegratable cleansing wipe as set forth in claim 35 further comprising an endpoint indicator.

48. The water disintegratable cleansing wipe as set forth in claim 35 wherein the endpoint indicator is selected from the group consisting of a coloring agent and a graphic.

49. The water disintegratable cleansing wipe as set forth in claim 35 wherein the filler fibers are selected from the group consisting of soft wood fibers, hard wood fibers, non-wood vegetable fibers, and combinations thereof.

50. The water disintegratable cleansing wipe as set forth in claim 35 further comprising from about 1% (by weight) to about 20% (by weight) of an abrasive agent.

51. The water disintegratable cleansing wipe as set forth in claim 50 wherein the abrasive agent is selected from the group consisting of pumice, silica, diatomaceous earth, polyethylene beads, nylon 12 beads, polymethacrylate polymers, nut shells, and clays.

52. The water disintegratable cleansing wipe as set forth in claim 35 further comprising from about 1% (by total weight) to about 5% (by total weight) of a foam stabilizer.

53. The water disintegratable cleansing wipe as set forth in claim 52 wherein the foam stabilizer is selected from the group consisting of alkanolamides, polyethylene glycols, polyols, PEG dimethicones, ethoxylated fatty alcohols, and combinations thereof.

\* \* \* \* \*